(12) United States Patent
Kobayashi et al.

(10) Patent No.: US 10,870,734 B2
(45) Date of Patent: *Dec. 22, 2020

(54) PRODUCTION METHOD FOR ORGANOPOLYSILOXANE EMULSION COMPOSITION

(71) Applicant: SHIN-ETSU CHEMICAL CO., LTD., Tokyo (JP)

(72) Inventors: Akihiro Kobayashi, Annaka (JP); Yuko Takada, Annaka (JP); Takuya Abe, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 101 days.

This patent is subject to a terminal disclaimer.

(21) Appl. No.: 15/757,521

(22) PCT Filed: Sep. 1, 2016

(86) PCT No.: PCT/JP2016/075666
§ 371 (c)(1),
(2) Date: Mar. 5, 2018

(87) PCT Pub. No.: WO2017/038938
PCT Pub. Date: Mar. 9, 2017

(65) Prior Publication Data
US 2018/0251607 A1 Sep. 6, 2018

(30) Foreign Application Priority Data
Sep. 4, 2015 (JP) .................. 2015-174346
Oct. 8, 2015 (JP) .................. 2015-199824

(51) Int. Cl.
C08J 3/05 (2006.01)
C08L 83/04 (2006.01)
C08G 77/06 (2006.01)
C08G 77/08 (2006.01)
C08G 77/16 (2006.01)
C09D 183/06 (2006.01)
A61K 8/06 (2006.01)
A61K 8/89 (2006.01)
C08K 5/42 (2006.01)
A61Q 5/00 (2006.01)
A61Q 5/02 (2006.01)
(Continued)

(52) U.S. Cl.
CPC .................. C08J 3/05 (2013.01); A61K 8/06 (2013.01); A61K 8/89 (2013.01); A61Q 5/002 (2013.01); A61Q 5/02 (2013.01); C08G 77/06 (2013.01); C08G 77/08 (2013.01); C08G 77/16 (2013.01); C08K 5/42 (2013.01); C08L 83/04 (2013.01); C09D 183/06 (2013.01); B29C 33/62 (2013.01); C08J 2383/06 (2013.01); D06M 15/643 (2013.01); D06M 2200/12 (2013.01); D06M 2200/50 (2013.01)

(58) Field of Classification Search
CPC ......... C08J 3/05; C08J 2383/06; C08L 83/04; C08G 77/06; C08G 77/16; C08G 77/08; C09D 183/06; A61K 8/06; A61K 8/89; A61Q 5/002; A61Q 5/02; C08K 5/42; B29C 33/62; D06M 15/643; D06M 2200/12; D06M 2200/50
See application file for complete search history.

(56) References Cited

U.S. PATENT DOCUMENTS 6,235,834 B1 * 5/2001 Gee .................. C08G 77/06
524/837
9,072,666 B2 7/2015 Ando
9,156,954 B2 10/2015 Cauvin et al.
(Continued)

FOREIGN PATENT DOCUMENTS

EP 1 069 149 A1 1/2001
EP 2 706 080 A1 3/2014
(Continued)

OTHER PUBLICATIONS

Extended European Search Report dated Mar. 1, 2019, in European Patent Application No. 16841967.9.
(Continued)

Primary Examiner — Abigail Vanhorn
(74) Attorney, Agent, or Firm — Birch, Stewart, Kolasch & Birch, LLP

(57) ABSTRACT

A production method for an organopolysiloxane emulsion composition, wherein (I) an emulsion composition is prepared from an organopolysiloxane (A) that is represented by formula (1) and that has an octamethylcyclotetrasiloxane content of 1,000 ppm or less $$HO(R^1_2SiO)_nH \qquad (1),$$

(wherein $R^1$ is H or a monovalent hydrocarbon group and n is a number that makes the viscosity, at 25° C., of the organopolysiloxane 200 mm²/s or more but less than 2,000 mm²/s), a surfactant (B) that is represented by formula (2) and that has an alkyl naphthalene skeleton $$R^2_a-C_{10}H_{(7-a)}-SO_3M \qquad (2),$$

(wherein $R^2$ is an alkyl group, M is $H^+$, an alkali metal ion, an alkali earth metal ion, $NH_4^+$, or a tertiary $NH_4^+$, and m is 1-3), and water (C-1), and wherein (II) water (C-2) is added as necessary and then emulsion polymerization is performed in the presence of an acid catalyst (D).

10 Claims, No Drawings

(51) Int. Cl.
*B29C 33/62* (2006.01)
*D06M 15/643* (2006.01)

(56) References Cited

U.S. PATENT DOCUMENTS

| | | | |
|---|---|---|---|
| 9,765,189 B2 * | 9/2017 | Kobayashi | C08L 83/04 |
| 2007/0244213 A1 * | 10/2007 | Wallace | A61K 8/066 |
| | | | 523/102 |
| 2014/0378553 A1 | 12/2014 | Ando | |
| 2015/0037272 A1 | 2/2015 | Ando | |

FOREIGN PATENT DOCUMENTS

| | | |
|---|---|---|
| JP | 34-2041 B | 4/1959 |
| JP | 41-13995 B | 8/1966 |
| JP | 2007-297533 A | 11/2007 |
| JP | 2009-126888 A | 6/2009 |
| JP | 2012-201867 A | 10/2012 |
| JP | 5382273 B1 | 1/2014 |
| JP | 2014-512418 A | 5/2014 |
| WO | WO 2013/153833 A1 | 10/2013 |
| WO | WO 2013/161500 A1 | 10/2013 |

OTHER PUBLICATIONS

International Search Report (PCT/ISA/210) issued in PCT/JP2016/075666, dated Oct. 4, 2016.
Written Opinion of the International Searching Authority (PCT/ISA/237) issued in PCT/JP2016/075666, dated Oct. 4, 2016.

* cited by examiner

PRODUCTION METHOD FOR ORGANOPOLYSILOXANE EMULSION COMPOSITION

TECHNICAL FIELD

The present invention relates to a method for producing an organopolysiloxane emulsion composition for use in products such as cosmetics, personal care compositions, home care compositions, mold release agents, slip agents, coating agents, textile finishes and resin modifiers.

BACKGROUND ART

It is desired that high-viscosity organopolysiloxanes intended for use in products such as cosmetics, personal care compositions, home care compositions, mold release agents, slip agents, coating agents, textile finishes and resin modifiers be rendered into emulsions having a small particle size and a good stability over time. However, when a high-viscosity organopolysiloxane is directly emulsified, the lower limit in the size of the emulsion particles is about several microns; achieving a smaller particle size is difficult, in addition to which the resulting emulsion has a poor stability over time. Accordingly, various methods for producing emulsions by emulsion polymerization have been investigated with the aim of obtaining emulsion particles endowed with a good stability over time.

For example, methods for carrying out the emulsion polymerization of a cyclic siloxane oligomer in an emulsified state by using a strong acid or a strong base are known (Patent Document 1: JP-B S34-2041; Patent Document 2: JP-B S41-13995). Using these methods, it is possible to obtain an emulsion having an emulsion particle size of 300 nm or less.

In recent years, there has come to be a desire for products in which the content of octamethylcyclotetrasiloxane is suppressed. In the methods described in Patent Documents 1 and 2, the organopolysiloxane included in the resulting emulsion is known to contain at least 40,000 ppm of octamethylcyclotetrasiloxane, and so methods for reducing this content are being investigated.

For example, methods are known wherein an organopolysiloxane which has a viscosity at 25° C. of from 3,000 to 100,000 mm$^2$/s and an octamethylcyclotetrasiloxane content of 1,000 ppm or less and which is capped at the ends of the molecular chain with silanol groups is emulsified, following which emulsion polymerization is carried out at a temperature below 40° C. and in the presence of an acid catalyst (Patent Document 3: JP No. 5382273). It is claimed that by using such a technique, an emulsion in which the amount of octamethylcyclotetrasiloxane included in the organopolysiloxane is 3,000 ppm or less can be obtained. However, in this method, because the monomer to be polymerized has a high viscosity of from 3,000 to 100,000 mm$^2$/s, a strong mechanical shear is required to reduce the particle size of an emulsion composition composed of this monomer. As a result, the emulsion that is obtained sometimes has a poor stability over time.

In addition, a method is known in which an organopolysiloxane that is capped at the ends of the molecular chain with silanol groups and has a viscosity at 25° C. of from 2,000 to 150,000 mm$^2$/s, water and a surfactant are emulsified, following which emulsion polymerization is carried out at a temperature of 16° C. or less in the presence of an acid catalyst (Patent Document 4: JP-A 2014-512418). With such methods, formation of the octamethylcyclotetrasiloxane that is included in this organopolysiloxane can be suppressed. However, a drawback of this method is that, because the monomer to be polymerized has a high viscosity of from 2,000 to 150,000 mm$^2$/s, a large amount of surfactant is required to obtain an emulsion composition having an average particle size of less than 1 μm.

Hence, there is a need to establish a method for producing an organopolysiloxane emulsion composition having a small particle size and good stability over time, which method suppresses the formation as a by-product of octamethylcyclotetrasiloxane included in the organopolysiloxane and does not use a large amount of surfactant.

PRIOR ART DOCUMENTS

Patent Documents

Patent Document 1: JP-B S34-2041
Patent Document 2: JP-B S41-13995
Patent Document 3: JP No. 5382273
Patent Document 4: JP-A 2014-512418

SUMMARY OF INVENTION

Technical Problem

It is therefore an object of this invention to provide a method for producing an organopolysiloxane emulsion composition having a small particle size and good stability over time, which method suppresses the formation as a by-product of the octamethylcyclotetrasiloxane included in the organopolysiloxane and does not use a large amount of surfactant.

Solution to Problem

The inventors have conducted extensive investigations in order to achieve these objects. As a result, they have discovered that (I) by using as the starting material an organopolysiloxane having silanol groups on the ends of the molecular chain and a viscosity at 25° C. of at least 200 mm$^2$/s and less than 2,000 mm$^2$/s and (2) by using a compound of general formula (2) as the surfactant for emulsifying the organopolysiloxane (component (A)), it is possible to suppress the formation as a by-product of the octamethylcyclotetrasiloxane included in the organopolysiloxane, to impart to the emulsion composition thus obtained a very small particle size of 500 nm or less without using a large amount of surfactant, and to give the composition a better stability over time than in the prior art. In this invention, the viscosity in mm$^2$/s units is the value at 25° C. as measured with an Ostwald viscometer.

Accordingly, the invention provides the following method for producing an organopolysiloxane emulsion composition, and the emulsion composition.

[1] A method for producing an emulsion composition of an organopolysiloxane, the method comprising the steps of:
(I) preparing an emulsion composition by emulsifying a mixture comprising
(A) 100 parts by weight of an organopolysiloxane of general formula (1) below which has an octamethylcyclotetrasiloxane content of not more than 1,000 ppm

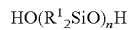

$$HO(R^1_2SiO)_nH \qquad (1)$$

(wherein each $R^1$ is independently a hydrogen atom or a substituted or unsubstituted monovalent hydrocarbon group of 1 to 20 carbon atoms, and n is a number such that the organopolysiloxane has a viscosity at 25° C. of at least 200 mm²/s and less than 2,000 mm²/s), (B) from 1 to 8 parts by weight of a surfactant of general formula (2) below having an alkylnaphthalene skeleton

$$R^2{}_a\text{—}C_{10}H_{(7-a)}SO_3M \qquad (2)$$

(wherein $R^2$ is a linear or branched alkyl group of 1 to 30 carbon atoms; M is a hydrogen ion, an alkali metal ion, an alkaline earth metal ion, an ammonium ion or a tertiary ammonium ion; and a is an integer from 1 to 3), and (C-1) from 1 to 10,000 parts by weight of water; and (II) after optionally adding to the resulting emulsion composition (C-2) from 0 to 10,000 parts by weight of water, carrying out emulsion polymerization at a temperature below 40° C. in the presence of (D) an acid catalyst (addition of the acid catalyst may be omitted when the surfactant (B) has a catalytic action), wherein the organopolysiloxane that forms has a viscosity at 25° C. of at least 300,000 mPa·s, the amount of octamethylcyclotetrasiloxane included in the organopolysiloxane is not more than 3,000 ppm, and the size of the resulting emulsion particles is not more than 500 nm.

[2] The production method of [1] wherein, when the emulsion composition is prepared in Step (I) using an emulsifier that employs a high pressure to reduce the size of the emulsion particles, the amount of component (C-1) water used per 100 parts by weight of component (A) is from 1 to 10,000 parts by weight.

[3] The production method of [1] wherein, when the emulsion composition is prepared in Step (I) using an emulsifier that employs shear forces to reduce the size of the emulsion particles, the amount of component (C-1) water used per 100 parts by weight of component (A) is from 1 to 10 parts by weight.

[4] The production method of any of [1] to [3], wherein the amount of the acid catalyst of component (D) present (including, when the surfactant of component (B) has a catalytic action and is encompassed by the acid catalyst of component (D), the amount of the surfactant of component (B) present) is at least 0.1 part by weight per 100 parts by weight of component (A).

[5] The production method of any of [1] to [4], wherein the surfactant (B) is a nonionic surfactant.

[6] The production method of any of [1] to [5] wherein, in Step (I), the particle size of the emulsion composition is set to not more than 500 nm.

[7] The production method of any of [1] to [6], wherein the emulsion polymerization step is carried out at a temperature below 25° C.

[8] The production method of any of [1] to [7], wherein the polymerization time in the emulsion polymerization step is not more than 48 hours.

[9] The organopolysiloxane emulsion composition production method of any of [1] to [8], wherein the particles of the target organopolysiloxane emulsion composition have an average size of not more than 200 nm.

[10] The organopolysiloxane emulsion composition production method of any of [1] to [9], wherein the organopolysiloxane in the target organopolysiloxane emulsion composition has a viscosity at 25° C. of at least 1,000,000 mPa·s.

[11] The organopolysiloxane emulsion composition production method of any of [1] to [10], wherein the amount of octamethylcyclotetrasiloxane included in the organopolysiloxane within the target organopolysiloxane emulsion composition is not more than 2,000 ppm.

Advantageous Effects of Invention

This invention makes it possible to obtain an emulsion composition which has a good stability over time, contains an organopolysiloxane having a viscosity at 25° C. of at least 300,000 mPa·s, has an amount of octamethylcyclotetrasiloxane included in the organopolysiloxane of not more than 3,000 ppm, and has an emulsion particle size of not more than 500 nm.

DESCRIPTION OF EMBODIMENTS

The starting materials used in the production method of the invention are described below.

<(A) Organopolysiloxane>

The organopolysiloxane serving as component (A) of the invention is an organopolysiloxane of general formula (1) below which has an octamethylcyclotetrasiloxane content of not more than 1,000 ppm.

$$HO(R^1{}_2SiO)_nH \qquad (1)$$

Here, each $R^1$ is independently a hydrogen atom or a substituted or unsubstituted monovalent hydrocarbon group of 1 to 20 carbon atoms, and n is a number such that the organopolysiloxane has a viscosity at 25° C. of at least 200 mm²/s and less than 2,000 mm²/s.

Each $R^1$ is independently a hydrogen atom or a substituted or unsubstituted monovalent hydrocarbon group of 1 to 20 carbon atoms. Unsubstituted monovalent hydrocarbon groups of 1 to 20 carbon atoms are exemplified by alkyl groups of 1 to 20 carbon atoms, cycloalkyl groups of 3 to 20 carbon atoms, alkenyl groups of 2 to 20 carbon atoms, aryl groups of 6 to 20 carbon atoms, and aralkyl groups of 7 to 20 carbon atoms. Illustrative examples include alkyl groups such as methyl, ethyl, propyl, butyl, pentyl, hexyl, heptyl, octyl, nonyl, decyl, dodecyl, tetradecyl, hexadecyl and octadecyl groups; cycloalkyl groups such as cyclopentyl and cyclohexyl groups; alkenyl groups such as vinyl, allyl and hexenyl groups; and aryl groups such as phenyl, tolyl and naphthyl groups. Substituted monovalent hydrocarbon groups of 1 to 20 carbon atoms are exemplified by the aforementioned monovalent hydrocarbon groups of 1 to 20 carbon atoms in which some of the hydrogen atoms are substituted with halogen atoms, amino groups, acryloxy groups, methacryloxy groups, epoxy groups, mercapto groups, carboxyl groups or hydroxyl groups. Preferred examples include monovalent hydrocarbon groups of 1 to 6 carbon atoms, such as methyl, ethyl, propyl, butyl and phenyl groups. The organopolysiloxane is even more preferably one in which at least 80% of all the $R^1$ groups are methyl groups.

The above n is a number such that the viscosity of the organopolysiloxane at 25° C. is at least 200 mm²/s and less than 2,000 mm²/s, preferably a number such that the viscosity is from 400 to 1,800 mm²/s, and more preferably a number such that the viscosity is from 600 to 1,600 mm²/s. When the viscosity is less than 200 mm²/s, the emulsion polymerization time must be lengthened in order to set the organopolysiloxane included in the target emulsion to the desired viscosity, or the amount of octamethylcyclotetrasiloxane that forms as a by-product during emulsion polymerization increases. On the other hand, when the viscosity is 2,000 mm²/s or more, a large amount of emulsifying agent is needed to make the particle size of the obtained target emulsion smaller.

The octamethylcyclotetrasiloxane content in the organopolysiloxane of component (A) is preferably not more than 1,000 ppm (by weight; the same applies below), and especially not more than 500 ppm. The octamethylcyclotetrasiloxane content has no particular lower limit, and may even be 0 ppm.

<(B) Surfactant>

The surfactant serving as component (B) is a surfactant of general formula (2) below having an alkylnaphthalene skeleton. One such surfactant may be used alone or two or more may be used in combination.

[Chem. 1]

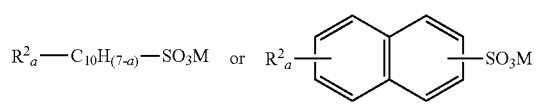

(2)

Here, $R^2$ is a linear or branched alkyl group of 1 to 30 carbon atoms, and M is a hydrogen ion, an alkali metal ion such as potassium or sodium, an alkaline earth metal ion such as magnesium or calcium, an ammonium ion, or a tertiary ammonium ion such as a triethanolammonium ion. a is an integer from 1 to 3. Also, —SO₃M generally bonds to the 1 position or 2 position on the naphthalene ring. The bonding position for $R^2$ is the 3 position, 4 position, 5 position, 6 position, 7 position or 8 position.

In general formula (2), $R^2$ is preferably a linear or branched alkyl group of 1 to 20 carbon atoms, and M is preferably, from the standpoint of the emulsifying effect, a sodium ion, a potassium ion, an ammonium ion or a triethanolammonium ion.

Examples of alkylnaphthalenesulfonic acids and salts thereof of general formula (2) include butylnaphthalenesulfonic acid, pentylnaphthalenesulfonic acid, decylnaphthalenesulfonic acid, dodecylnaphthalenesulfonic acid, tetradecylnaphthalenesulfonic acid, hexadecylnaphthalenesulfonic acid, isopropylnaphthalenesulfonic acid, bisisopropylnaphthalenesulfonic acid, trisisopropylnaphthalenesulfonic acid, and salts thereof.

The amount of component (B) used per 100 parts by weight of component (A) may be set to from 1 to 8 parts by weight, and is preferably from 2 to 7 parts by weight, and more preferably from 3 to 6 parts by weight.

Component (B) may include a nonionic surfactant. Such a surfactant may be of one type used alone, or two or more may be used together. In cases where a nonionic surfactant is used, the amount included is preferably from 0.1 to 8 parts by weight per 100 parts by weight of component (A).

Nonionic surfactants are exemplified by polyoxyalkylene alkyl ethers, polyoxyalkylene alkyl phenyl ethers, polyoxyethylene-polyoxypropylene alkyl ethers, polyoxyalkylene alkyl esters, polyoxyalkylene sorbitan alkyl esters, polyethylene glycols, polypropylene glycols and diethylene glycols. One type may be used alone, or two or more may be suitably selected and used together. Of these, nonionic surfactants of general formula (3) below are preferred.

(3)

Here, $R^3$ is a linear or branched alkyl group of 8 to 30 carbon atoms, EO represents an ethylene oxide group and PO represents a propylene oxide group, these being arranged randomly or as blocks. p and q are each independently integers from 0 to 100, with the proviso that p+q>0, and preferably that 50≥p+q≥1. In particular, in general formula (3), $R^3$ is preferably a linear or branched alkyl group of 8 to 13 carbon atoms. Also, it is preferable for p and q to be independently from 0 to 25 and to satisfy the relationship 0<p+q≤50.

Specific examples of nonionic surfactants of general formula (3) include polyoxyethylene octyl ether, polyoxyethylene-polyoxypropylene octyl ether, polyoxyethylene nonyl ether, polyoxyethylene decyl ether, polyoxyethylene-polyoxypropylene decyl ether, polyoxyethylene lauryl ether, polyoxyethylene-polyoxypropylene lauryl ether, polyoxyethylene tridecyl ether, polyoxyethylene-polyoxypropylene tridecyl ether and polyoxyethylene cetyl ether. Use can also be made of a reactive surfactant having a functional group. These surfactants may be of one type used alone, or two or more may be used together. The alkyl group above may be linear or may be branched.

<(C) Water>

The water serving as component (C) is (C-1) used in Step (I) and, optionally, (C-2) used in Step (II).

In Step (I), the amount of water used as component (C-1) is from 1 to 10,000 parts by weight per 100 parts by weight of component (A), and varies according to the type of emulsifier used when reducing the size of the emulsion particles.

For example, in cases where a high-pressure homogenizer which uses high pressure to reduce the size of the emulsion particles (e.g., an emulsifier which pressurizes a treatment liquid to a high pressure or ultrahigh pressure and passes it through a slit to obtain shear forces, or an emulsifier which causes pressurized treatment liquids to obliquely collide with each other at ultrahigh speed and thereby atomize) is employed, the amount of component (C-1) used per 100 parts by weight of component (A) is preferably from 1 to 10,000 parts by weight, more preferably from 4 to 6,000 parts by weight, and even more preferably from 6 to 4,000 parts by weight.

Alternatively, in cases where an emulsifier such as a homogenizing disperser which uses shear forces to reduce the size of the emulsion particles (an emulsifier which causes a circular disk having saw-teeth on the outer periphery to rotate at high speed so as to obtain shear forces), a homogenizing mixer (an emulsifier having a stator installed on the outer periphery and a rotor installed at the interior that is made to rotate at high speed, thereby generating shear forces), or a colloid mill (an emulsifier in which the various ingredients are fed to a gap between a disk that rotates at high speed and a stationary disk, thereby generating shear forces) is employed, the amount of component (C-1) used per 100 parts by weight of component (A) is preferably from 1 to 10 parts by weight, more preferably from 2 to 8 parts by weight, and even more preferably from 4 to 6 parts by weight. Here, when more than 10 parts by weight is added, it may be difficult to obtain an emulsion composition in which the emulsion particles have a small size of 1 μm or less; when less that 1 part by weight is added, it may be difficult to obtain an oil-in-water (O/W) emulsion.

In Step (II), component (C-2) may be added or may not be added, with the amount thereof preferably being not more than 10,000 parts by weight (i.e., from 0 to 10,000 parts by weight) per 100 parts by weight of component (A). When component (C-2) is added, the amount thereof is preferably from 1 to 1,000 parts by weight, and especially from 1 to 500 parts by weight. It is generally preferable for the water serving as component (C-2) to be added when using an emulsifier such as a homogenizing disperser, a homogenizing mixer or a colloid mill.

<(D) Acid Catalyst>

When component (B) has a catalytic action, component (D) may not be necessary. In cases where component (D) is used, a single type may be used alone or two or more may be suitably combined and used together.

Component (D) is exemplified by the following ingredients.

(1) Alkylsulfuric acids of general formula (4) and alkylbenzenesulfonic acids of general formula (5):

$$R^4OSO_3H \quad (4)$$

(wherein $R^4$ is a linear or branched alkyl group of 6 to 30 carbon atoms)

$$R^4\text{—}C_6H_4\text{—}SO_3H \quad (5)$$

(wherein $R^4$ is, as defined in general formula (4), a linear or branched alkyl group of 6 to 30 carbon atoms).

In general formulas (4) and (5), $R^4$ is preferably a linear or branched alkyl group of 6 to 12 carbon atoms.

Specific examples of alkylsulfuric acids of general formula (4) include hexylsulfuric acid, octylsulfuric acid, decylsulfuric acid, dodecylsulfuric acid, tetradecylsulfuric acid, hexadecylsulfuric acid, octadecylsulfuric acid and eicosylsulfuric acid.

Specific examples of alkylbenzenesulfonic acids of general fdrmula (5) include hexylbenzenesulfonic acid, octylbenzenesulfonic acid, decylbenzenesulfonic acid, dodecylbenzenesulfonic acid, tetradecylbenzenesulfonic acid and hexadecylbenzenesulfonic acid.

(2) Higher Fatty Acids:

Specific examples include lauric acid, stearic acid, oleic acid and linolenic acid.

(3) Polyoxyethylene alkyl ether sulfuric acids of general formula (6):

$$R^4O(EO)_s(PO)_tSO_3H \quad (6)$$

Here, $R^4$ is, as defined in general formula (4), a linear or branched alkyl group of 6 to 30 carbon atoms. EO represents an ethylene oxide group and PO represents a propylene oxide group, these being arranged randomly or as blocks. s and t are each independently integers from 0 to 100, with the proviso that s+t>0, and especially that 50≥s+t≥1.

Specific examples include polyoxyethylene hexyl ether sulfuric acid, polyoxyethylene octyl ether sulfuric acid, polyoxyethylene decyl ether sulfuric acid, polyoxyethylene dodecyl ether sulfuric acid, polyoxyethylene tetradecyl ether sulfuric acid, polyoxyethylene hexadecyl ether sulfuric acid, polyoxyethylene octadecyl ether sulfuric acid and polyoxyethylene eicosyl ether sulfuric acid.

(4) Polyoxyethylene alkyl phenyl ether sulfuric acids of general formula (7) below:

$$R^4\text{—}C_6H_4\text{—}O(EO)_s(PO)_tSO_3H \quad (7)$$

Here, $R^4$ is, as defined in general formula (4), a linear or branched alkyl group of 6 to 30 carbon atoms. EO, PO and s and t are as defined in general formula (6). That is, EO represents an ethylene oxide group and PO represents a propylene oxide group, these being arranged randomly or as blocks. s and t are each independently integers from 0 to 100, with the proviso that s+t>0, and especially that 50≥s+t≥1.

Specific examples include polyoxyethylene hexyl phenyl ether sulfuric acid, polyoxyethylene octyl phenyl ether sulfuric acid, polyoxyethylene decyl phenyl ether sulfuric acid, polyoxyethylene dodecyl phenyl ether sulfuric acid, polyoxyethylene tetradecyl phenyl ether sulfuric acid and polyoxyethylene hexadecyl phenyl ether sulfuric acid.

(5) BrøNsted Acids:

Examples include hydrochloric acid, hydrobromic acid, sulfuric acid, chlorosulfonic acid, phosphoric acid, orthophosphoric acid, metaphosphoric acid, polyphosphoric acid, boric acid, nitric acid, benzenesulfonic acid, methanesulfonic acid, trifluoromethanesulfonic acid, carboxylic acids, chloroacetic acid, trichloroacetic acid, acetic acid, acrylic acid, benzoic acid, trifluoroacetic acid, citric acid, crotonic acid, formic acid, fumaric acid, maleic acid, malonic acid, tannic acid, itaconic acid, lactic acid, tartaric acid, oxalic acid, phthalic acid, succinic acid, cation exchange resins, acidic zeolites, acid-active fuller's earth and acid-active carbon black.

The amount of component (D) used (including, when the surfactant of component (B) has a catalytic action and is encompassed by the acid catalyst of component (D), the amount of component (B) used) is preferably at least 0.1 part by weight, more preferably at least 0.3 part by weight, and even more preferably at least 0.5 part by weight, per 100 parts by weight of component (A). When the amount is less than 0.1 part by weight, the polymerization rate may become extremely slow. The amount of component (D) has no particular upper limit, although it is preferably not more than 125 parts by weight.

The production method of the invention is described below.

<Step (I)>

An emulsion composition is prepared by emulsifying a mixture containing components (A), (B) and (C). Here, emulsification may be carried out using an emulsifier such as a homogenizing disperser, a homogenizing mixer, a colloid mill, a line mixer, a universal mixer, an ultra mixer, a planetary mixer, a combination mixer or a high-pressure homogenizer. An emulsifier which reduces the size of the emulsion particles using shear forces, such as a homogenizing disperser, a homogenizing mixer or a colloid mill, is preferred; a homogenizing disperser is even more preferred.

In this step, the emulsification temperature is preferably from 1 to 80° C. When component (B) has a catalytic action, a cyclization reaction also proceeds at the same time, and so emulsification is preferably carried out at a temperature of below 40° C. Should emulsification be carried out at a temperature of 40° C. or more, the production of octamethylcyclotetrasiloxane may increase. Accordingly, the temperature is preferably less than 30° C., and more preferably less than 25° C.

In Step (I), the mixture is mixed under the application of high shear forces until the size of the emulsion particles in the emulsion composition becomes preferably 500 nm or less, more preferably 300 nm or less, and even more preferably 200 nm or less. The smaller the size of the emulsion particles obtained in Step (I), the higher the rate of polymerization in Step (II), thus shortening the polymerization time. Because the size of the emulsion particles in the emulsion composition obtained in Step (I) is 500 nm or less, the ultimate size of the emulsion particles obtained in the next step also is 500 nm or less. In this invention, the size of the emulsion particles is the median diameter, as measured with a model LA-920 laser diffraction/scattering type particle size analyzer (Horiba, Ltd.).

<Step (II)>

After optionally adding and dispersing (C-2) water in the resulting emulsion composition, component (D) is added at a temperature of below 40° C. and emulsion polymerization is carried out until the viscosity of the organopolysiloxane at 25° C. becomes at least 300,000 mPa·s, as measured with a rotational viscometer.

In cases where component (C-2) has thus been added to the emulsion composition, emulsification/dispersion may be additionally carried out thereafter with an emulsifier such as a high-pressure homogenizer.

When the emulsion composition is emulsion polymerized, it is recommended that the polymerization step be carried out at a temperature below 40° C. for not more than 48 hours. When polymerization is carried out at a temperature above 40° C., octamethylcyclotetrasiloxane formation may increase. The polymerization temperature is thus preferably below 25° C., and more preferably below 15° C. When the polymerization time exceeds 48 hours, the formation of octamethylcyclotetrasiloxane as a by-product may increase. The polymerization time is thus preferably from 1 to 40 hours, and more preferably from 5 to 30 hours.

The organopolysiloxane produced by emulsion polymerization in step (II) has a viscosity at 25° C., as measured with a rotational viscometer, of at least 300,000 mPa·s, preferably at least 450,000 mPa·s, more preferably at least 600,000 mPa·s, and most preferably at least 1,000,000 mPa·s. The viscosity is not subject to any particular upper limit, although it is generally not more than 20,000,000 mPa·s.

<Other Treatment>

Once polymerization has ended, the resulting emulsion composition is generally neutralized with a basic substance. Examples of the basic substance include sodium hydroxide, potassium hydroxide, sodium carbonate, sodium bicarbonate, and amine compounds such as triethanolamine and triethylamine.

The silicone concentration may be adjusted at this time by adding water. Also, additives such as preservatives and fungicides may be added in order to increase the shelf stability of the emulsion composition.

In weatherstripping, fabric finish and resin modification applications, by adding an alkoxysilane such as $R^5{}_3Si(OR^6)$, $R^5{}_2Si(OR^6)_2$ or $R^5Si(OR^6)_3$ in Step (I) in which emulsification is carried out, in Step (II) in which emulsion polymerization is carried out, or to the emulsion composition after carrying out neutralization, it is possible to introduce various functional groups onto the resulting organopolysiloxane chain. Here, $R^5$ is a hydrogen atom or a substituted or unsubstituted monovalent hydrocarbon group of 1 to 20, and preferably 1 to 6, carbon atoms, illustrative examples of which include methyl, ethyl, propyl, butyl and phenyl groups. $R^6$ is the same or a different alkyl group of 1 to 20 carbon atoms or is a hydrogen atom.

In the emulsion composition which is obtained by the inventive method of production and includes an organopolysiloxane having a viscosity at 25° C. of at least 300,000 mPa·s, the viscosity of the organopolysiloxane in the emulsion composition is at least 300,000 mPa·s, preferably at least 450,000 mPa·s, and more preferably at least 600,000 mPa·s. The viscosity is not subject to any particular upper limit, although it is generally not more than 10,000,000 mPa·s.

The average size of the emulsion particles in the emulsion composition is preferably not more than 500 nm, and more preferably not more than 200 nm. Although not subject to any particular lower limit, the average particle size is generally at least about 30 nm. By way of this invention, a very fine emulsion composition in which the average size of the emulsion particles is not more than 300 nm can be obtained. The average size of the emulsion particles is the median diameter obtained by the laser diffraction/scattering method.

The content of octamethylcyclotetrasiloxane included in the organopolysiloxane is not more than 3,000 ppm, preferably not more than 2,000 ppm, and more preferably not more than 1,000 ppm. Although not subject to any particular lower limit, the content is 0 ppm or more.

The content of decamethylcyclopentasiloxane included in the organopolysiloxane is preferably not more than 3,000 ppm, more preferably not more than 2,000 ppm, and even more preferably not more than 1,000 ppm. Although not subject to any particular lower limit, the content is 0 ppm or more.

EXAMPLES

The invention is illustrated more fully below by way of Examples and Comparative Examples, although these Examples are not intended to limit the invention. All references to "parts" are by weight. Viscosities are values measured at 25° C. with an Ostwald viscometer. The naphthalenesulfonates in the Examples below are mixtures in which —SO₃M is bonded to the 1 position or the 2 position on the naphthalene ring.

Example 1

5 parts of (B) sodium pentylnaphthalenesulfonate (in general formula (2), $R^2$ is a pentyl group, M is a sodium ion, and a=1) and 6 parts of (C-1) water mixed with 100 parts of (A) an organopolysiloxane having silanol groups at the ends of the molecular chain and a viscosity of 700 mm²/s (in general formula (1), $R^1$ is a methyl group; octamethylcyclotetrasiloxane content, ≤50 ppm), and were emulsified with a homogenizing disperser. Next, 85.4 parts of (C-2) water was added to the resulting first emulsion and dilution/dispersion was carried out with a homogenizing mixer. Concentrated hydrochloric acid (D), 1.2 parts, was then added and emulsion polymerization was carried out at 10° C. for 22 hours. This was followed by the addition of 2.4 parts of triethanolamine to the resulting emulsion and dilution/dispersion with a homogenizing mixer, thereby giving an emulsion composition. The results are shown in Table 1.

Example 2

5 parts of (B) sodium trisisopropylnaphthalenesulfonate. (in general formula (2), $R^2$ is an isopropyl group, M is a sodium ion, and a=3) and 6 parts of (C-1) water were mixed with 100 parts of (A) an organopolysiloxane having silanol groups at the ends of the molecular chain and a viscosity of 700 mm²/s (in general formula (1), $R^1$ is a methyl group; octamethylcyclotetrasiloxane content, ≤50 ppm), and emulsified with a homogenizing disperser. Next, 86 parts of (C-2) water was added to the resulting first emulsion and dilution/dispersion was carried out with a homogenizing mixer. Concentrated hydrochloric acid (D), 0.6 part, was then added and emulsion polymerization was carried out at 10° C. for 22 hours. This was followed by the addition of 2.4 parts of triethanolamine to the resulting emulsion and dilution/dispersion with a homogenizing mixer, thereby giving an emulsion composition. The results are shown in Table 1.

Example 3

5 parts of (B) pentylnaphthalenesulfonic acid (in general formula (2), $R^2$ is a pentyl group, M is a hydrogen atom, and a=1) and 6 parts of (C-1) water were mixed with 100 parts of (A) an organopolysiloxane having silanol groups at the ends of the molecular chain and a viscosity of 1,500 mm$^2$/s (in general formula (1), R$^1$ is a methyl group; octamethylcyclotetrasiloxane content, ≤50 ppm), and emulsified with a homogenizing disperser. Next, 85.8 parts of (C-2) water was added to the resulting first emulsion, after which dilution/dispersion was carried out with a homogenizing mixer, and emulsion polymerization was subsequently carried out at 10° C. for 17 hours. This was followed by the addition of 3.2 parts of triethanolamine to the resulting emulsion and dilution/dispersion with a homogenizing mixer, thereby giving an emulsion composition. The results are shown in Table 1.

Comparative Example 1

4 parts of (B) polyoxyethylene tridecyl ether (EO, 10 moles) and 6 parts of (C-1) water mixed with 100 parts of an organopolysiloxane having silanol groups at the ends of the molecular chain and a viscosity of 5,000 mm$^2$/s (in general formula (1), R$^1$ is a methyl group; octamethylcyclotetrasiloxane content, ≤50 ppm), and emulsified with a homogenizing mixer. Next, 83.6 parts of (C-2) water was added to the resulting first emulsion, after which dilution/dispersion was carried out, and emulsion polymerization was subsequently carried out at 0° C. for 15 hours. This was followed by the addition of 2.4 parts of triethanolamine to the resulting emulsion and dilution/dispersion with a homogenizing mixer, thereby giving an emulsion composition. The results are shown in Table 1.

Comparative Example 2

A mixture of 9.1 parts of triethanolamine and 10.5 parts of Marlon AS 3 (alkylbenzenesulfonic acid) was prepared beforehand. To this were added 100 parts of an organopolysiloxane having silanol groups at the end of the molecular chain and a viscosity of 2,500 mm$^2$/s and 4.1 parts of water, and emulsification was carried out with a change-can mixer. Next, 57.3 parts of water was added to the resulting emulsion, after which dilution/dispersion was carried out with a change-can mixer, thereby preparing a masterbatch emulsion.

The temperature of 100 parts of this masterbatch emulsion was lowered to 21° C., and 15.2 parts of 10 wt % sulfuric acid was added so as to start an emulsion polymerization reaction. The reaction temperature was then lowered to 10° C. over 4 hours, following which emulsion polymerization was carried out at 10° C. for 10 hours. This was followed by the addition of 4 parts of triethanolamine to the resulting emulsion and dilution/dispersion with a homogenizing mixer, thereby giving an emulsion composition. The results are shown in Table 1.

Comparative Example 3

2 parts of (B) polyoxyethylene tridecyl ether (EO, 10 moles), 3.5 parts of sodium dodecylbenzenesulfonate and 6 parts of (C-1) water were mixed with 100 parts of (A) an organopolysiloxane having silanol groups at the ends of the molecular chain and a viscosity of 150 mm$^2$/s (in general formula (1), R$^1$ is a methyl group; octamethylcyclotetrasiloxane content, ≤50 ppm), and emulsified with a homogenizing disperser. Next, 84.9 parts of (C-2) water was added to the resulting first emulsion and dilution/dispersion was carried out with a homogenizing mixer. Concentrated hydrochloric acid (D), 1.2 parts, was then added and emulsion polymerization was carried out at 10° C. for 32 hours. This was followed by the addition of 2.4 parts of triethanolamine to the resulting emulsion and dilution/dispersion with a homogenizing mixer, thereby giving an emulsion composition. The results are shown in Table 1.

The following properties of the emulsion compositions obtained in the above Examples were measured or evaluated by the methods shown below. The results are shown in Table 1.

[Average Particle Size of Emulsion]

This is the median diameter, as measured with a model LA-920 laser diffraction/scattering type particle size analyzer (Horiba, Ltd.).

[Viscosity of Organopolysiloxane]

Isopropyl alcohol, 300 g, was added under stirring to 300 g of the prepared emulsion composition. Only the organopolysiloxane that separated out was collected and dried at 105° C. for 3 hours, following which the viscosity at 25° C. was measured with a rotational viscometer.

[Octamethylcyclotetrasiloxane Content in Organopolysiloxane]

The emulsion composition, 0.1 g, was extracted (3 hours of shaking) with 10 mL of acetone containing 20 ppm (weight basis) of tetradecane as an internal standard and then left to stand overnight, following which the acetone layer was collected and the octamethylcyclotetrasiloxane was quantitatively determined by gas chromatographic analysis.

[Stability of Emulsion]

The emulsion composition, 100 g, was placed in a 100 mL glass jar and left to stand for three months at 50° C., following which the appearance was examined. When the emulsion formed a single uniform phase and no separation was observable, the stability was rated as "○." When separation into two phases was observed, the stability was rated as "x."

TABLE 1

|  | Polymerization temperature (° C.) | Polymerization time (hr) | Average particle size (nm) | Viscosity (mPa · s) | D$_4$ content (ppm) | Stability (50° C., 3 months) |
|---|---|---|---|---|---|---|
| Example 1 | 10 | 22 | 150 | 2,300,000 | 700 | ○ |
| Example 2 | 10 | 22 | 160 | 2,100,000 | 750 | ○ |
| Example 3 | 10 | 17 | 140 | 2,000,000 | 550 | ○ |
| Comparative Example 1 | 0 | 15 | 150 | 2,200,000 | 1,200 | X |
| Comparative Example 2 | 10 | 14 | 190 | 1,700,000 | 880 | X |
| Comparative Example 3 | 10 | 32 | 150 | 2,200,000 | 2,600 | X |

Note:
D$_4$: Octamethylcyclotetrasiloxane

INDUSTRIAL APPLICABILITY

The inventive composition has an excellent stability and is very pleasant to use, making it particularly useful for cosmetics and household goods. For example, it can be used in hair care products such as shampoos and rinses.

It can also be used as a protective material for furniture and sundry articles, as a mold release agent for molds used when manufacturing rubber products and plastic products, and as a textile finish for imparting water repellency and softness to fibers.

The invention claimed is:

1. A method for producing an organopolysiloxane oil-in-water emulsion composition, the method comprising the steps of:
   (I) preparing an emulsion composition by emulsifying a mixture comprising
   (A) 100 parts by weight of an organopolysiloxane of general formula (1) below which has an octamethylcyclotetrasiloxane content of not more than 1,000 ppm $$HO(R^1_2SiO)_nH \qquad (1)$$

(wherein each $R^1$ is independently a hydrogen atom or a substituted or unsubstituted monovalent hydrocarbon group of 1 to 20 carbon atoms, and n is a number such that the organopolysiloxane has a viscosity at 25° C. of at least 200 mm$^2$/s and less than 2,000 mm$^2$/s),
   (B) from 1 to 8 parts by weight of a surfactant of general formula (2) below having an alkylnaphthalene skeleton $$R^2_a\text{—}C_{10}H_{(7-a)}\text{—}SO_3M \qquad (2)$$

(wherein $R^2$ is a linear or branched alkyl group of 1 to 30 carbon atoms; M is a hydrogen ion, an alkali metal ion, an alkaline earth metal ion, an ammonium ion or a tertiary ammonium ion; and a is an integer from 1 or 3), and
   (C-1) from 1 to 10,000 parts by weight of water; and
   (II) after optionally adding to the resulting emulsion composition
   (C-2) from 0 to 10,000 parts by weight of water, carrying out emulsion polymerization at a temperature below 40° C. in the presence of
   (D) an acid catalyst, which is optional when component (B) is catalytic,
   wherein the organopolysiloxane that forms has a viscosity at 25° C. of at least 300,000 mPa·s, the amount of octamethylcyclotetrasiloxane included in the organopolysiloxane that forms is not more than 3,000 ppm, and the size of the resulting emulsion particles is not more than 500 nm,
   wherein the organopolysiloxane emulsion composition that forms after Step (II) is stable at 50° C. for at least 3 months.

2. The production method of claim 1 wherein, when the emulsion composition is prepared in Step (I) using an emulsifier that employs a high pressure to reduce the size of the emulsion particles, the amount of component (C-1) water used per 100 parts by weight of component (A) is from 1 to 10,000 parts by weight.

3. The production method of claim 1 wherein, when the emulsion composition is prepared in Step (I) using an emulsifier that employs shear forces to reduce the size of the emulsion particles, the amount of component (C-1) water used per 100 parts by weight of component (A) is from 1 to 10 parts by weight.

4. The production method of claim 1, wherein the amount of the acid catalyst of component (D) present (including, when the surfactant of component (B) has a catalytic action and is encompassed by the acid catalyst of component (D), the amount of the surfactant of component (B) present) is at least 0.1 part by weight per 100 parts by weight of component (A).

5. The production method of claim 1 wherein, in Step (I), the particle size of the emulsion composition is set to not more than 500 nm.

6. The production method of claim 1, wherein the emulsion polymerization step is carried out at a temperature below 25° C.

7. The production method of claim 1, wherein the polymerization time in the emulsion polymerization step is not more than 48 hours.

8. The organopolysiloxane emulsion composition production method of claim 1, wherein the particles of the organopolysiloxane emulsion composition that forms after Step (II) have an average size of not more than 200 nm.

9. The organopolysiloxane emulsion composition production method of claim 1, wherein the organopolysiloxane that forms in the organopolysiloxane emulsion composition that forms after Step (II) has a viscosity at 25° C. of at least 1,000,000 mPa·s.

10. The organopolysiloxane emulsion composition production method of claim 1, wherein the amount of octamethylcyclotetrasiloxane included in the organopolysiloxane that forms within the organopolysiloxane emulsion composition that forms after Step (II) is not more than 2,000 ppm.

* * * * *